US007227016B2

(12) United States Patent
Ravikumar et al.

(10) Patent No.: US 7,227,016 B2
(45) Date of Patent: Jun. 5, 2007

(54) PROCESS FOR THE SYNTHESIS OF OLIGOMERIC COMPOUNDS

(75) Inventors: Vasulinga T. Ravikumar, Carlsbad, CA (US); Muthiah Manoharan, Weston, MA (US); Daniel C. Capaldi, Carlsbad, CA (US); Achim Krotz, San Diego, CA (US); Douglas L. Cole, Half Moon Bay, CA (US); Andrei Guzaev, Vista, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/024,958

(22) Filed: Dec. 28, 2004

(65) Prior Publication Data

US 2005/0137390 A1 Jun. 23, 2005

Related U.S. Application Data

(63) Continuation of application No. 10/940,360, filed on Sep. 14, 2004, which is a continuation of application No. 10/760,940, filed on Jan. 20, 2004, now Pat. No. 7,041,816, which is a continuation of application No. 10/232,881, filed on Aug. 30, 2002, now Pat. No. 6,858,715, which is a continuation of application No. 09/288,679, filed on Apr. 9, 1999, now Pat. No. 6,465,628.

(60) Provisional application No. 60/118,564, filed on Feb. 4, 1999.

(51) Int. Cl.
C07H 21/00 (2006.01)

(52) U.S. Cl. .................. 536/25.31; 536/25.34

(58) Field of Classification Search ............... 536/23.1, 536/24.3, 24.5, 25.31, 25.33, 25.34

See application file for complete search history.

(56) References Cited

U.S. PATENT DOCUMENTS

| 3,687,808 | A | 8/1972 | Merigan et al. |
|---|---|---|---|
| 4,415,732 | A | 11/1983 | Caruthers et al. |
| 4,417,046 | A | 11/1983 | Hsiung |
| 4,426,517 | A | 1/1984 | Hsiung |
| 4,458,066 | A | 7/1984 | Caruthers et al. |
| 4,500,707 | A | 2/1985 | Caruthers et al. |
| 4,668,777 | A | 5/1987 | Caruthers et al. |
| 4,672,110 | A | 6/1987 | Letsinger |
| 4,725,677 | A | 2/1988 | Köster et al. |
| 4,835,263 | A | 5/1989 | Nguyen et al. |
| 4,973,679 | A | 11/1990 | Caruthers et al. |
| 5,132,418 | A | 7/1992 | Caruthers et al. |
| RE34,069 | E | 9/1992 | Köster et al. |
| 5,210,264 | A | 5/1993 | Yau |
| 5,212,295 | A | 5/1993 | Cook |
| 5,362,866 | A | 11/1994 | Arnold, Jr. |
| 5,514,789 | A | 5/1996 | Kempe |
| 5,589,586 | A | 12/1996 | Holmberg |
| 5,686,599 | A | 11/1997 | Tracz |
| 5,750,672 | A | 5/1998 | Kempe |
| 5,804,683 | A | 9/1998 | Usman et al. |
| 5,936,077 | A | 8/1999 | Pfleiderer et al. |
| 5,977,343 | A | 11/1999 | Tracz |
| 6,054,576 | A | 4/2000 | Bellon et al. |
| 6,162,909 | A | 12/2000 | Bellon et al. |
| 6,166,197 | A | 12/2000 | Cook et al. |
| 6,172,209 | B1 | 1/2001 | Manoharan et al. |
| 6,271,358 | B1 | 8/2001 | Manoharan et al. |
| 6,303,773 | B1 | 10/2001 | Bellon et al. |
| 6,465,628 | B1 | 10/2002 | Ravikumar et al. |
| 6,649,751 | B2 | 11/2003 | Usman et al. |
| 6,664,388 | B2 | 12/2003 | Nelson |
| 6,673,918 | B2 | 1/2004 | Bellon et al. |
| 6,858,715 | B2 * | 2/2005 | Ravikumar et al. ........ 536/23.1 |
| 2002/0072593 | A1 | 6/2002 | Sinha |
| 2003/0181712 | A1 | 9/2003 | Nelson |

FOREIGN PATENT DOCUMENTS

| DE | 196 27 898 | 1/1998 |
|---|---|---|
| EP | 0 514 513 B1 | 1/1996 |
| EP | 1 028 124 A2 | 8/2000 |
| JP | 62-42997 | 2/1987 |
| WO | WO 97/29780 | 8/1997 |
| WO | WO 00/46231 | 8/2000 |
| WO | WO 01/96358 | 12/2001 |

OTHER PUBLICATIONS

Alul, R. H. et al, "Oxalyl-CPG: a labile support for synthesis of sensitive oligonucleotide derivatives," *Nucleic Acids Res.* (1991) 19(7): 1527-1532.
Bannwarth, W., "Synthesis of Oligodeoxynucleotides by the Phosphite-Triester Method Using Dimer Units and Different Phosphorus-Protecting Goups," *Helv. Chim. Acta* (1985) 68: 1907-1913.
Beaucage, S. L. et al., "Advances in the Synthesis of Oligonucleotides by the Phosphoramidite Approach," *Tetrahedron* (1992) 48(12): 2223-2311.
Boal, J. H. et al., "Cleavage of oligodeoxyribonucleotides from controlled-pore glass supports and their rapid deprotection by gaseous amines," *Nucleic Acids Res.* (1996) 24(15): 3115-3117.
Brown, T. et al., "Modern machine-aided methods of oligodeoxyribonucleotide synthesis," *Oligonucleotides and Analogs A Practical Approach* (1991), Chp. 1, Eckstein, F. (ed), IRL Press, Oxford, pp. 1-24.
Cook, P. D., "Medicinal chemistry of antisense oligonucleotides—future opportunities," *Anti-Cancer Drug Design* (1991) 6: 585-607.

(Continued)

Primary Examiner—S. Anna Jiang
Assistant Examiner—L. E. Crane
(74) Attorney, Agent, or Firm—Isis Patent Department

(57) ABSTRACT

Synthetic processes are provided wherein oligomeric compounds are prepared having phosphodiester, phosphorothioate, phosphorodithioate, or other covalent linkages. The oligomers have substantially reduced exocyclic adducts deriving from acrylonitrile or related contaminants.

12 Claims, No Drawings

OTHER PUBLICATIONS

Caruthers, M. H., "DNA Synthesis for Nonchemists: The Phosphoramidite Method on Silica Supports," *Synthesis and Applications of DNA and RNA* (1987), Narang, S. A. (ed.). Academic Press, Inc., Orlando, pp. 47-94.

Delgado, C. et al., "The Uses and Properties of PEG-Linked Proteins," *Crit. Rev. In Therap. Drug Carriers Sys.* (1992) 9(3,4): 249-304.

Efimov, V. A. et al., "New efficient sulfurizing reagents for the preparation of oligodeoxyribonucleotide phosphorothioate analoques," *Nucleic Acids Res.* (1995) 23(20): 4029-4033.

Englisch, U. et al., "Chemically Modified Oligonucleotides as Probes and Inhibitors," *Angew. Chem. Int. Ed. Eng.* (1991) 30(6): 613-629.

Eritja, R. et al., "A Synthetic Procedure for the Preparation of Oligonucleotides Without Using Ammonia and Its Application for the Synthesis of Oligonucleotides Containing O-4-Alkyl Thymidines," *Tetrahedron* (1992) 48(20): 4171-4182.

Geiger, L. E. et al., "Metabolism of Acrylonitrile by Isolated Rat Hepatocytes," *Cancer Res.* (1983) 43(7): 3080-3087.

Griffey, R. H. et al., "2'-O-Aminopropyl Ribonucleotides: A Zwitterionic Modification that Enhances the Exonuclease Resistance and Biological Activity of Antisense Oligonucleotides," *J. Med. Chem.* (1996) 39(26): 5100-5109.

Hogy, L. L. et al., "In Vivo Interaction of Acrylonitrile and 2-Cyanoethylene Oxide with DNA in Rats," *Cancer Res.* (1986) 46(8): 3932-3938.

Hsiung, H. et al., "Further improvements on the phosphodiester synthesis of deoxyriboligonucleotides and the oligonucleotide directed site-specific mutagenesis of E.coli lipoprotein gene," *Nucleic Acids Research* (1983) 11(10): 3227-3239. (May 25, 1983).

Iyer, R. P. et al., "The Automated Synthesis of Sulfur-Containing Oligodeoxyribonucleotides Using 3H-1,2-Benzodithiol-3-one 1,1-Dioxide as a Sulfer-Transfer Reagent," *J. Am. Chem. Soc.* (1990) 55(15): 4693-4699.

Iyer, R. P. et al., "3H-1,2-Benzodithiole-3-one 1,1-Dioxide as an Improved Sulfurizing Reagent in the Solid-Phase Synthesis of Oligodeoxyribonucleoside Phophorothioates," *J. Am. Chem. Soc.* (1990) 112(3): 1253-1254.

Kamer, P. C. J. et al., "An Efficient Approach Toward the Synthesis of Phosphorothioate Diesters via the Schönberg Reaction," *Tetrahedron Letts.* (1989) 30(48): 6757-6760.

Kroschwitz, J. I., "Polynucleotides," *Concise Encyclopedia of Polymer Science and Engineering* (1990) John Wiley & Sons, New York, pp. 858-859.

Kumar, G. et al., "Improvements in Oligodeoxyribonucleotide Synthesis: Methyl N,N-Dialkylphosphoramidite Dimer Units for Solid Support Phosphite Methodology," *J. Org. Chem.* (1984) 49(25): 4902-4912.

Martin, P., "Ein neuer Zugang zu 2'-O-Alkylribonucleosiden und Eigenschaften deren Oligonucleotide," *Helvetica Chimica Acta* (1995) 78: 486-504.

Miura, K. et al., "Blockwise Mechanical Synthesis of Oligonucleotides by the Phosphoramidite Method," *Chem. Pharm. Bull.* (1987) 35(2): 833-836.

Mullah, B. et al., "Automated Synthesis of Double Dye-Labeled Oligonucleotides using Tetramethylrhodamine (TAMRA) Solid Supports," *Tetra Letts.* (1997) 38(33): 5751-5754.

Ohtsuka, E. et al., "Studies on Transfer Ribonucleic Acids and Related Compounds. XVI. Synthesis of Ribooligonucleotides Using a Photosensitive o-Nitrobenzyl Protection for the 2'-Hydroxyl Group," *Chemical & Pharmaceutical Bulletin* (1997) 25(5): 949-959. (May 1997).

Ohtsuka, E. et al., "Synthesis of E.coli tRNA$_f^{Met}$ fragments", *Nucleic Acids Research Symposium Series*, Special Publication No. 2 (1976), pp. s77-s80.

Ouchi, T. et al., "Synthesis and Antitumor Activity of Poly(Ethylene Glycol)s Linked to 5-Fluorouracil via a Urethane or Urea Bond," *Drug Des. Disc.* (1992) 9: 93-105.

Pon, R. T. et al., "Hydroquinone-O, O'-diacetic acid ('Q-linker') as a replacement for succinyl and oxalyl linker arms in solid phase oligonucleotide synthesis," *Nucleic Acids Res.*(1997) 25(18): 3629-3635.

Rao, M. V. et al., "Dibenzoyl Tetrasulphide—A Rapid Sulphur Transfer Agent in the Synthesis of Phosphorothioate Analogues of Oligonucleotides," *Tetra. Letts.* (1992) 33(33): 4839-4842.

Ravasio, N. et al., "Selective Hydrogenations Promoted by Copper Catalysts. 1. Chemoselectivity, Regioselectivity, and Stereoselectivity in the Hydrogenation of 3-Substituted Steroids," *J. Org. Chem.* (1991) 56(13): 4329-4333.

Sanghvi, Y.S., "Heterocyclic Base Modifications in Nucleic acids and their Applications in Antisense Oligonucleotides," *Antisense Research and Applications* (1993) Chp. 15, CRC Press, Boca Raton, pp. 273-288.

Schulhof, J. C. et al., "Facile Removal of New Base Protecting Groups Useful in Oligonucleotide Synthesis," *Tetrahedron Letts.* (1987) 28(1): 51-54.

Secrist, III, J. A. et al., "Synthesis and Biological Activity of 4'-Thionucleosides," *10th International Roundtable: Nucleosides, Nucleotides and their Biological Applications*, Sep. 16-20, 1992, Abstract 21, Park City, Utah, 40.

Sobkowski, M. et al., "The Reactions of H-Phosphonates with Bifunctional Reagents. Part V. Functionalization of Support-Bound Oligonucleotides and Synthesis of Non-Radioactive Hybridization Probes," *Nucleosides & Nucleotides* (1998) 17(1-3): 253-267.

Solomon, J. J. et al., "Direct Alkylation of Calf Thymus DNA by Acrylonitrile. Isolation of Cyanoethyl Adducts of Guanine and Thymine and Carboxyethyl Adducts of Adenine and Cytosine," *Environ. Health Persp.* (1985) 62: 227-230.

Solomon, J. J. et al., "DNA Adducts of Propylene Oxide and Acrylonitrile Epoxide: Hydrolytic Deamination of 3-Alkyl-dCyd to 3-Alkyl-dUrd," *Environ. Health Persp.* (1989) 81: 19-22.

Solomon, J. J. et al., "In Vitro Alkylation of Calf Thymus DNA by Acrylonitrile. Isolation of Cyanoethyl-Adducts of Guanine and Thymine and Carboxyethyl-Adducts of Adenine and Cytosine," *Chem.-Biol. Interactions* (1984) 51: 167-190.

Stec, W. J. et al., "Bis(O,O-Diisopropoxy Phophinothioyl) Disulfide—A Highly Efficient Sulfurizing Reagent for Cost-Effective Synthesis of Oligo(Nucleoside Phosphorothioate)s," *Tetrahedron Letts.* (1993) 34(33): 5317-5320.

Stevens, R. D. et al., "Application of electrospray ionization mass spectrometry for analysis of haemoglobin adducts with acrylonitrile," *Biochem. Soc. Trans.* (1994) 22: 543-547.

Uziel, M. et al., "DNA adduct formation by 12 chemicals with populations potentially suitable for molecular epidemiological studies," *Mutation Res.* (1992) 277:35-90.

Vu, H. et al., "Internucleotide Phosphite Sulfurization with Tetraethylthiuram Disulfide. Phosphorothioate Oligonucleotide Synthesis via Phosphoramidite Chemistry," *Tetrahedron Letts.* (1991) 32(26): 3005-3008.

Wolter, A. et al., "Polymer Support Oligonucleotide Synthesis XX: Synthesis of a Henhectacosa Deoxynucleotide by use of a Dimeric Phophoramidite Synthon," *Nucleosides Nucleotides* (1986) 5(1): 65-77.

Wright, P. et al., "Large Scale Synthesis of Oligonucleotides via Phosphoramidite Nucleosides and a High-loaded Polystyrene Support," *Tetrahedron Letts.* (1993) 34(21): 3373-3376.

Xu, Q. et al., "Use of 1,2,4-dithiazolidine-3,5-dione (DtsNH) and 3-ethoxy-1,2,4-dithiazoline-5-one (EDITH) for synthesis of phosphorothioate-containing oligodeoxyribonucleotides," *Nucl. Acids Res.* (1996) 24(9): 1602-1607.

Xu, Q. et al., "Efficient introduction of phosphorothioates into RNA oligonucleotides by 3-ethoxy-1,2,4-dithiazoline-5-one (EDITH)," *Nucleic Acids Res.* (1996) 24(18): 3643-3644.

Yates, J. M. et al., "Characterization of phosphodiester adducts produced by the reaction of cyanoethylene oxide with nucleotides," *Carcinogensis* (1994) 15(2): 277-283.

Yates, J. M. et al., "Characterization of an adduct and its degradation product produced by the reaction of cyanoethylene oxide with deoxythymidine and DNA," *Carcinogenesis* (1993) 14(7): 1363-1369.

Zhang, Z. et al., "Solid Phase Synthesis of Oligonucleotide Phosphorothioate Analogues Using 3-Methyl-1,2,4-dithiazolin-5-one (MEDITH) as a New Sulfur-Transfer Reagent," *Tetrahedron Lett.* (1999) 40(11): 2095-2098.

* cited by examiner

PROCESS FOR THE SYNTHESIS OF OLIGOMERIC COMPOUNDS

CROSS REFERENCE TO RELATED APPLICATIONS

This application is a continuation of allowed patent application Ser. No. 10/940,360, filed on Sep. 14, 2004, published as U.S. patent application Ser. No. 2005-0137391, which is a continuation of patent application Ser. No. 10/760,940, filed on Jan. 20, 2004, now U.S. Pat. No. 7,041,816, which is a continuation of U.S. application Ser. No. 10/232,881, filed on Aug. 30, 2002, now U.S. Pat. No. 6,858,715, which is a continuation of patent application Ser. No. 10/288,679, filed on Apr. 9, 1999, now U.S. Pat. No. 6,465,628, and claims priority benefit of U.S. provisional application Ser. No. 60/118,564, filed on Feb. 4, 1999, entitled "Improved Synthesis of Oligonucleotides." The entire contents of each of the foregoing patents and patent applications are incorporated herein by reference.

FIELD OF THE INVENTION

This invention relates to improved methods for the preparation of oligomeric compounds having phosphodiester, phosphorothioate, phosphorodithioate or other linkages. In preferred embodiments, the methods of the invention provide oligomers that have reduced amounts of unwanted side-products.

BACKGROUND OF THE INVENTION

Antisense and other oligonucleotide therapies have gone beyond academic publications to the level of approved drug as shown by the recent FDA approval of an antisense oligonucleotide therapeutic for ocular cytomegalovirus infections. More and more oligonucleotides are entering the clinic for the treatment of a variety of diseases such as inflammation, cancer, viral disease and others. There is an urgent need for improved methods for the synthesis of oligonucleotides in high quantity and with high quality. Solid phase chemistry is the present method of choice. Typical synthons now used are O-cyanoethyl protected nucleoside phosphoamidite monomers. At the end of the synthesis, the oligonucleotide product is treated typically with 30% aqueous ammonium hydroxide to deprotect the cyanoethyl groups on the phosphorothioate backbone as well as exocyclic amino groups. During this deprotection step, one molecule of acrylonitrile is produced for every cyanoethyl group present.

It is now known that acrylonitrile is a rodent carcinogen and that, at pH 7, it can react with T, dC, dG, dA and dI, resulting in the formation of a variety of adducts. See, Solomon et al., *Chem.-Biol. Interactions*, 51, 167-190 (1984). it is greatly desired to eliminate these impurities in synthesis of oligonucleotides, especially phosphorothioate oligonucleotides.

Eritja et al. (*Tetrahedron*, 48, 4171-4182 (1992)) report the prevention of acrylonitrile adduct formation of nucleobase moieties during deprotection of β-cyanoethyl protected oligomers by 40% triethylamine in pyridine for 3 hours followed by treatment with 0.5 M DBU/pyridine. However, as will be seen infra, their conditions failed to eliminate adduct formation to a suitable extent.

Given the demand for oligonucleotides and analogs thereof for clinical use, and the known toxicity of acrylonitrile nucleobase adducts, methods of preparing phosphate linked oligomers having reduced amount of such adducts are greatly desired. The present invention is directed to this, as well a other, important ends.

SUMMARY OF THE INVENTION

The present invention provides an improved method for the preparation of phosphate-linked oligomers that have significantly reduced amounts of exocyclic nucleobase adduct resulting from the products of removal of phosphorus protecting groups. In one aspect of the invention, methods are provided comprising:

a) providing a sample containing a plurality of oligomers of the Formula I:

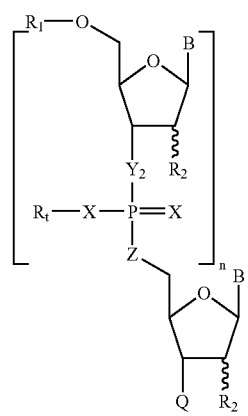

wherein:
$R_1$ is H or a hydroxyl protecting group;
B is a naturally occurring or non-naturally occurring nucleobase that is optionally protected at one or more exocyclic hydroxyl or amino groups;
$R_2$ has the Formula III or IV:

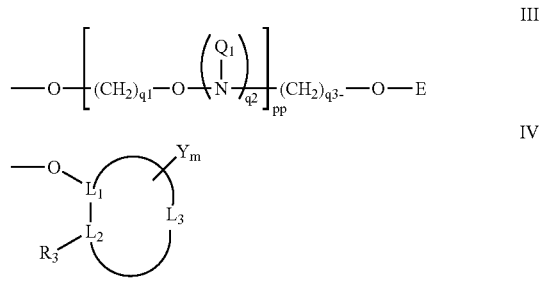

wherein
E is $C_1$-$C_{10}$ alkyl, $N(Q_1)(Q_2)$ or $N=C(Q_1)(Q_2)$;
each $Q_1$ and $Q_2$ is, independently, H, $C_1$-$C_{10}$ alkyl, dialkylaminoalkyl, a nitrogen protecting group, a tethered or untethered conjugate group, a linker to a solid support, or $Q_1$ and $Q_2$, together, are joined in a nitrogen protecting group or a ring structure that can include at least one additional heteroatom selected from N and O;
$R_3$ is $OX_1$, $SX_1$, or $N(X_1)_2$;
each $X_1$ is, independently, H, $C_1$-$C_8$ alkyl, $C_1$-$C_8$ haloalkyl, $C(=NH)N(H)Z_8$, $C(=O)N(H)Z_8$ or $OC(=O)N(H)$ $Z_8$;
$Z_8$ is H or $C_1$-$C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $O(Q_1)$, halo, $S(Q_1)$, or CN;

each $q_1$ is, independently, from 2 to 10;
each $q_2$ is, independently, 0 or 1;
m is 0, 1 or 2;
pp is from 1 to 10; and
$q_3$ is from 1 to 10 with the proviso that when pp is 0, $q_3$ is greater than 1;

$R_t$ is a phosphorus protecting group of formula:

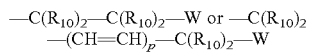

each $R_{10}$ is independently H or lower alkyl;
W is an electron withdrawing group;
p is 0 to 3;
each $Y_2$ is independently, O, $CH_2$ or NH;
each Z is independently O or S;
each X is independently O or S;
Q is a linker connected to a solid support, —OH or O—Pr where Pr is a hydroxyl protecting group; and
n is 1 to about 100;

b) contacting said sample with a deprotecting reagent for a time and under conditions sufficient to remove substantially said $R_t$ groups from said oligomers; and c) reacting said oligomers with a cleaving reagent;

wherein said deprotecting reagent comprises at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents.

Preferably, the methods further comprises a washing step before step (c).

In some preferred embodiments, Q is a linker connected to a solid support. In further preferred embodiments, said deprotecting reagent does not cleave said oligomers from said solid support.

In some preferred embodiments, the deprotecting reagent comprises an aliphatic amine, which is preferably triethylamine or piperidine.

In further preferred embodiments, the deprotecting agent comprises a haloalkyl solvent or a cyanoalkyl solvent, which is preferably acetonitrile or methylene chloride.

In particularly preferred embodiments, the phosphorus protecting group is —$CH_2$—$CH_2$—C≡N or —$CH_2$—(CH=CH)$_p$—$CH_2$—C≡N, where p is an integer from 1 to 3, with —$CH_2$—$CH_2$—C≡N or —$CH_2$—CH=CH—$CH_2$—C≡N being preferred, and —$CH_2$—$CH_2$—C≡N being particularly preferred.

In some preferred embodiments, the deprotecting reagent or cleaving reagent further comprises a scavenger, which is preferably a purine, a pyrimidine, inosine, a pyrrole, an imidazole, a triazole, a mercaptan, a beta amino thiol, a phosphine, a phosphite, a diene, a urea, a thiourea, an amide, an imide, a cyclic imide, a ketone, an alkylmercaptan, a thiol, ethylene glycol, a substituted ethylene glycol, 1-butanethiol, S-(2-amino-4-thiazolylmethyl)isothiourea hydrochloride, 2-mercaptoethanol, 3,4-dichlorobenzylamine, benzylamine, benzylamine in the presence of carbon disulfide, hydroxylamine, 2-phenylindole, n-butylamine, diethyl ester of acetaminomalonic acid, ethyl ester of N-acetyl-2-cyanoglycine, 3-phenyl-4-(o-fluorophenyl)-2-butanone, 3,4-diphenyl-2-butanone, desoxybenzoin, N-methoxyphthalimide, p-sulfobenzenediazonium chloride, or p-sulfamidobenzenediazonium chloride.

In some preferred embodiments, the scavenger is a resin containing a suitable scavenging molecule bound thereto. Exemplary scavenger resins include polymers having free thiol groups and polymers having free amino groups, for example a polymer-bound amine resin wherein the amine is selected from benzylamine, ethylenediamine, diethylamine triamine, tris(2-aminoethyl)amine, methylamine, methylguanidine, polylysine, oligolysine, Agropore™ $NH_2$HL, Agropore™ $NH_2$LL (available from Aldrich Chem. Co. St. Louis. Mo.), 4-methoxytrityl resin, and thiol 2-chlorotrityl resin.

In some preferred embodiments, Q is —OH or O—Pr.

In some preferred embodiments, the cleaving reagent comprises an aqueous methanolic solution of a Group I or Group II metal carbonate, preferably aqueous methanolic $CaCO_3$. In further preferred embodiments, the cleaving reagent comprises an aqueous metal hydroxide. In yet further preferred embodiments, the cleaving reagent comprises a phase transfer catalyst. Preferred phase transfer catalysts include quaternary ammonium salts, quaternary phosphonium salts, crown ethers and cryptands (i.e., crown ethers which are bicyclic or cycles of higher order). It is more preferred that the phase transfer catalyst be t-$Bu_4N^+OH$, or t-$Bu_4N^+F^-$.

In further preferred embodiments, the cleaving reagent comprises $NaNH_2$.

In preferred embodiments, the oligomers produced by the methods of the invention have from 0.001% to about 1% acrylonitrile adduct, with from about 0.1% to about 1% acrylonitrile adduct being more preferred, from about 0.1% to about 0.75% acrylonitrile adduct being even more preferred, and from about 0.1% to about 0.5% acrylonitrile adduct being even more preferred. In even more preferred embodiments, the oligomers are substantially free of detectable acrylonitrile adduct.

In some preferred embodiments, steps b) and c) are performed simultaneously.

In some particularly preferred embodiments, Q is a linker connected to a solid support; said aliphatic amine is triethylamine or piperidine; said solvent is acetonitrile or ethylene chloride; and said phosphorus protecting group is —$CH_2$—$CH_2$—C≡N or —$CH_2$—CH=CH—$CH_2$—C≡N, and wherein the deprotecting reagent, said cleaving reagent, or both preferably further comprises a scavenger.

In further preferred embodiments, the deprotecting reagent comprises a secondary alkyl amine which is preferably piperidine, and said cleaving reagent comprises an alkali metal carbonate, which is preferably potassium carbonate.

Also provided by the present invention are methods for deprotecting a phosphate-linked oligomer, said oligomer having a plurality of protected phosphorus linkages of Formula II:

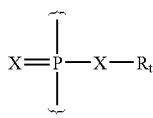

wherein:
Each X is O or S;
$R_t$ is a phosphorus protecting group of the formula:

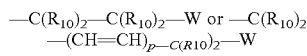

each $R_{10}$ is independently H or lower alkyl;
W is an electron withdrawing group;
p is 1 to 3;

comprising:
(a) providing a sample containing a plurality of said phosphate linked oligomers;
(b) contacting said oligomers with a deprotecting reagent for a time and under conditions sufficient to remove substantially all of said $R_t$ groups from said oligomers, said deprotecting reagent containing at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents; and
(c) reacting said oligomers with a cleaving reagent.

Preferably, the methods further comprises a washing step before step (c).

In some preferred emboidiments, the oligomers are in solution. In other preferred embodiments, the oligomers are linked to a solid support.

In some preferred embodiments, said deprotecting reagent does not cleave said oligomers from said solid support.

In some preferred embodiments, the deprotecting reagent comprises an aliphatic amine, which is preferably triethylamine or piperidine.

In further preferred embodiments, the deprotecting agent comprises a haloalkyl solvent or a cyanoalkyl solvent, which is preferably acetonitrile or methylene chloride.

In particularly preferred embodiments, the phosphorus protecting group is —CH$_2$—CH$_2$—C≡N or —CH$_2$—(CH=CH)$_p$—CH$_2$—C≡N, where p is an integer from 1 to 3, with —CH$_2$—CH$_2$—C≡N or —CH$_2$—CH=CH—CH$_2$—C≡N being preferred, and with —CH$_2$—CH$_2$—C≡N being particularly preferred.

In some preferred embodiments, the deprotecting reagent or cleaving reagent further comprises a scavenger, which is preferably a purine, a pyrimidine, inosine, a pyrrole, an imidazole, a triazole, a mercaptan, a beta amino thiol, a phosphine, a phosphite, a diene, a urea, a thiourea, an amide, an imide, a cyclic imide, a ketone, an alkylmercaptan, a thiol, ethylene glycol, a substituted ethylene glycol, 1-butanethiol, S-(2-amino-4-thiazolylmethyl)isothiourea hydrochloride, 2-mercaptoethanol, 3,4-dichlorobenzylamine, benzylamine, benzylamine in the presence of carbon disulfide, hydroxylamine, 2-phenylindole, n-butylamine, diethyl ester of acetaminomalonic acid, ethyl ester of N-acetyl-2-cyanoglycine, 3-phenyl-4-(o-fluorophenyl)-2-butanone, 3,4-diphenyl-2-butanone, desoxybenzoin, N-methoxyphthalimide, p-sulfobenzenediazonium chloride, or p-sulfamidobenzenediazonium chloride.

In some preferred embodiments, the scavenger is a resin containing a suitable scavenging molecule bound thereto. Exemplary scavenger resins include polymers having free thiol groups and polymers having free amino groups, for example a polymer-bound amine resin wherein the amine is selected from benzylamine, ethylenediamine, diethylamine triamine, tris(2-aminoethyl)amine, methylamine, methyiguanidine, polylysine, oligolysine, Agropore™ NH$_2$HL, Agropore™ NH$_2$LL, 4-methoxytrityl resin, and thiol 2-chlorotrityl resin.

In some preferred embodiments, the cleaving reagent comprises an aqueous methanolic solution of a Group I or Group II metal carbonate, preferably aqueous methanolic potassium carbonate. In further preferred embodiments, the cleaving reagent comprises an aqueous metal hydroxide. In yet further preferred embodiments, the cleaving reagent comprises a phase transfer catalyst. Preferred phase transfer catalysts include quaternary ammonium salts, quaternary phosphonium salts, crown ethers and cryptands (i.e., crown ethers which are bicyclic or cycles of higher order). It is more preferred that the phase transfer catalyst be t-Bu$_4$N$^+$OH, or t-Bu$_4$N$^+$F$^-$.

In further preferred embodiments, the cleaving reagent comprises NaNH$_2$.

In preferred embodiments, the produced by the methods of the invention oligomers have from about 0.001% to about 1% acrylonitrile adduct, with from about 0.001% to about 0.5% acrylonitrile adduct being more preferred, from about 0.001% to about 0.1% acrylonitrile adduct being even more preferred, and from about 0.001% to about 0.05% acrylonitrile adduct being even more preferred. In even more preferred embodiments, the oligomers are substantially free of acrylonitrile adduct.

In some preferred embodiments, steps b) and c) are performed simultaneously.

In some particularly preferred embodiments, said aliphatic amine is triethylamine or piperidine; said solvent is acetonitrile or methylene chloride; and said phosphorus protecting group is —CH$_2$—CH$_2$—C≡N or —CH$_2$—CH=CH—CH$_2$—C≡N, and wherein the deprotecting reagent, said cleaving reagent, or both preferably further comprises a scavenger.

In further preferred embodiments, the deprotecting reagent comprises a secondary alkyl amine which is preferably piperidine, and said cleaving reagent comprises an alkali metal carbonate, which is preferably potassium carbonate.

Also provided by the present invention are methods for deprotecting a phosphate-linked oligomer, said oligomer having a plurality of protected phosphorus linkages of Formula II:

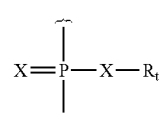

wherein:
Each X is O or S;
$R_t$ is a phosphorus protecting group of formula:

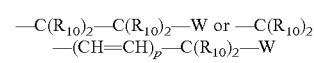

each $R_{10}$ is independently H or lower alkyl;

W is an electron withdrawing group;
p is 1 to 3;

comprising:

(a) providing a sample containing a plurality of said phosphate linked oligomers;

(b) contacting said oligomers with a deprotecting reagent for a time and under conditions sufficient to remove substantially all of said $R_t$ groups from said oligomers;

(c) washing said deprotected oligomers with a washing reagent comprising at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents; and (d) reacting said oligomers with a cleaving reagent.

In some preferred embodiments, the oligomers are in solution. In other preferred embodiments, the oligomers are linked to a solid support.

In some preferred embodiments, the deprotecting reagent does not cleave said oligomers from said solid support.

In further preferred embodiments, the deprotecting reagent comprises an aliphatic amine, which is preferably triethylamine or piperidine. In still further preferred embodiments, the deprotecting agent comprises a haloalkyl solvent or a cyanoalkyl solvent which is preferably acetonitrile or methylene chloride.

In particularly preferred embodiments, the phosphorus protecting group is —CH$_2$—CH$_2$—C≡N or —CH$_2$—(CH=CH)$_p$—CH$_2$—C≡N, where p is an integer from 1 to 3, with —CH$_2$—CH$_2$—C≡N or —CH$_2$—CH=CH—CH$_2$—C≡N being preferred, and with —CH$_2$—CH$_2$—C≡N being particularly preferred.

In some preferred embodiments, the deprotecting reagent, the cleaving reagent or the washing reagent further comprises a scavenger, which is preferably a purine, a pyrimidine, inosine, a pyrrole, an imidazole, a triazole, a mercaptan, a beta amino thiol, a phosphine, a phosphite, a diene, a urea, a thiourea, an amide, an imide, a cyclic imide a ketone, an alkylmercaptan, a thiol, ethylene glycol, a substituted ethylene glycol, 1-butanethiol, S-(2-amino-4-thiazolylmethyl)isothiourea hydrochloride, 2-mercaptoethanol, 3,4-dichlorobenzylamine, benzylamine, benzylamine in the presence of carbon disulfide, hydroxylamine, 2-phenylindole, n-butylamine, diethyl ester of acetaminomalonic acid, ethyl ester of N-acetyl-2-cyanoglycine, 3-phenyl-4-(o-fluorophenyl)-2-butanone, 3,4-diphenyl-2-butanone, desoxybenzoin, N-methoxyphthalimide, p-sulfobenzenediazonium chloride, or p-sulfamidobenzenediazonium chloride.

In some preferred embodiments, the scavenger is a resin containing a suitable scavenging molecule bound thereto. Exemplary scavenger resins include polymers having free thiol groups and polymers having free amino groups, for example a polymer-bound amine resin wherein the amine is selected from benzylamine, ethylenediamine, diethylamine triamine, tris(2-aminoethyl)amine, methylamine, methylguanidine, polylysine, oligolysine, Agropore™ NH$_2$HL, Agropore™ NH$_2$LL, 4-methoxytrityl resin, and thiol 2-chlorotrityl resin.

In some preferred, embodiments, the cleaving reagent comprises an aqueous methanolic solution of a Group I or Group II metal carbonate, preferably aqueous methanolic potassium carbonate. In further preferred embodiments, the cleaving reagent comprises an aqueous metal hydroxide. In yet further preferred embodiments, the cleaving reagent comprises a phase transfer catalyst. Preferred phase transfer catalysts include quaternary ammonium salts, quaternary phosphonium salts, crown ethers and cryptands (i.e., crown ethers which are bicyclic or cycles of higher order). It is more preferred that the phase transfer catalyst be t-Bu$_4$N$^+$ OH, or t-Bu$_4$N$^+$F$^-$.

In further preferred embodiments, the cleaving reagent comprises NaNH$_2$.

In preferred embodiments, the oligomers produced by the methods of the invention have from 0.001% to about 1% acrylonitrile adduct, with from about 0.1% to about 1% acrylonitrile adduct being more preferred, from about 0.1% to about 0.75% acrylonitrile adduct being even more preferred, and from about 0.1% to about 0.5% acrylonitrile adduct being even more preferred. In even more preferred embodiments, the oligomers are substantially free of is detectable acrylonitrile adduct.

In some particularly preferred embodiments, said aliphatic amine is triethylamine or piperidine; said solvent is acetonitrile or methylene chloride; and said phosphorus protecting group is —CH$_2$—CH$_2$—C≡N or —CH$_2$—CH=CH—CH$_2$—C≡N, and wherein the deprotecting reagent, the washing reagent, the cleaving reagent, or each preferably further comprise a scavenger.

In further preferred embodiments, the deprotecting reagent comprises a secondary alkyl amine which is preferably piperidine, and said cleaving reagent comprises an alkali metal carbonate, which is preferably potassium carbonate.

The present invention also provides methods for deprotecting a phosphate-linked oligomer, said oligomer having a plurality of phosphorus linkages of Formula II:

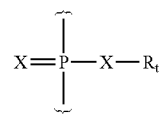

II wherein:
Each X is O or S;
$R_t$ is a phosphorus protecting group of the formula:

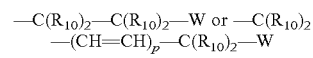

each $R_{10}$ is independently H or lower alkyl;
W is an electron withdrawing group;
p is 1 to 3;

comprising:

(a) providing a sample containing a plurality of said phosphate linked oligomers; and (b) contacting said oligomers with a deprotecting reagent for a time and under conditions sufficient to remove substantially all of said $R_t$ groups from said oligomers, said deprotecting reagent comprising gaseous ammonia.

Also provided in accordance with the present invention are compositions comprising phosphodiester, phosphorothioate, or phosphorodithioate oligonucleotides produced by the methods of the invention.

The present invention also provides compositions comprising phosphodiester, phosphorothioate, or phosphorodithioate oligonucleotides, said oligonucleotides having from about 0.001% to about 1% acrylonitrile adduct, with from about 0.1% to about 1% acrylonitrile adduct being more preferred, from about 0.1% to about 0.75% acrylonitrile adduct being even more preferred, and from about 0.1% to about 0.5% acrylonitrile adduct being even more preferred. In particularly preferred embodiments, compositions comprising phosphodiester, phosphorothioate, or phosphorodithioate oligonucleotides, said oligonucleotides are provided that are substantially free of detectable acrylonitrile adduct.

The present invention also provides composition comprising oligonucleotides that are substantially free of acrylonitrile adduct prepared by the methods of the invention.

Further provided in accordance with the present invention are methods of preparing a sample of a phosphate linked oligonucleotide having a substantially reduced content of acrylonitrile adduct comprising:

(a) providing a sample containing a plurality of oligomers, said oligomers having a plurality of phosphorus protecting groups;

(b) contacting said oligomers with a deprotecting agent to remove substantially all of said phosphorus protecting groups from said oligomers;

said deprotecting reagent comprising at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents;

(c) optionally washing said oligomers; and (d) reacting said oligomers with a cleaving reagent. Further provided in accordance with the present invention are methods of preparing a sample of a phosphate linked oligonucleotide having a substantially reduced content of acrylonitrile adduct comprising:

(a) providing a sample containing a plurality of oligomers, said oligomers having a plurality of phosphorus protecting groups;

(b) contacting said oligomers with a deprotecting agent to remove substantially all of said phosphorus protecting groups from said oligomers;

(c) washing said oligomers with a washing reagent, said washing reagent comprising at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents; and (d) reacting said oligomers with a cleaving reagent.

DESCRIPTION OF PREFERRED EMBODIMENTS

The present invention provides methods for the preparation of oligomeric compounds having phosphodiester, phosphorothioate, phosphorodithioate, or other internucleoside linkages, and to composition produced by the methods.

The methods of the invention are applicable to both solution phase and solid phase chemistries. Representative solution phase techniques are described in U.S. Pat. No. 5,210,264, which is assigned to the assignee of the present invention. in some preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humans Press, Totowa, N.J., 1993. A preferred synthetic solid phase synthesis utilizes phosphoraroidites as activated phosphate compounds. In this technique, a 5'-protected phosphoramidite monomer is reacted with a free hydroxyl on the growing oligorner chain to produce an intermediate phosphite compound, which is subsequently oxidized to the $P^V$ state using standard methods. This technique is commonly used for the synthesis of several types of linkages including phosphodiester, phosphorothioate, and phosphorodithioste linkages.

Typically, the first step in such a process is attachment of a first monomer or higher order subunit containing a protected 5'-hydroxyl to a solid support, usually through a linker, using standard methods and procedures known in the art. See for example, *Oligonucleotides And Analogues A Practical Approach*, Eckstein, F. Ed., IRL Press, N.Y., 1991. The support-bound monomer or higher order first synthon is then treated to remove the 5'-protecting group. The solid support bound monomer is then reacted with an activated phosphorous monomer or higher order synthon which is typically a nucleoside phosphoramidite, which is suitably protected at the phosphorus atom, and at any vulnerable exocyclic amino or hydroxyl groups. Typically, the coupling of the phosphoramidite to the support bound chain is accomplished under anhydrous conditions in the presence of an activating agent such as, for example, 1H-tetrazole, 5-(4-nitrophenyl)-1H-tetrazole, or diisopropylamino tetrazolide.

The resulting linkage is a phosphite or thiophosphite, which is subsequently oxidized prior to the next iterative cycle. Choice of oxidizing or sulfurizing agent will determine whether the linkage will be oxidized or sulfurized to a phosphodiester, thiophosphodiester, or a dithiophosphodiester linkage.

At the end of the synthetic regime, the support-bound oligomeric chain is typically treated with strong base (e.g., 30% aqueous ammonium hydroxide) to cleave the completed oligonucleotide form the solid support, and to concomitantly remove phosphorus protecting groups (which are typically β-cyanoethyl protecting groups) and exocyclic nucleobase protecting groups. Without intending that the invention be bound by any particular theory, it is believed that the loss of the cyanoethyl phosphorus protecting group occurs via a β-elimination mechanism, which produces acrylonitrile as a product. The acrylonitrile is believed to react in a Michael addition with nucleobase exocyclic amine and/or hydroxyl moieties, and in particular the $N^3$ position of thymidine residues, to form deleterious adducts. The methods of the present invention significantly reduce the content of such adducts formed during the removal of phosphorus protecting groups that are capable of participating in such adduct-forming addition reactions.

Thus, in one aspect, the present invention provides synthetic methods comprising:

a) providing a sample containing a plurality of oligomers of the Formula I:

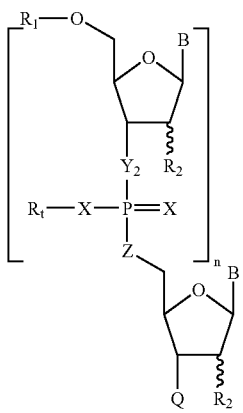

wherein:

$R_1$ is H or a hydroxyl protecting group;

B is a naturally occurring or non-naturally occurring nucleobase that is optionally protected at one or more exocyclic hydroxyl or amino groups;

$R_2$ has the Formula III or IV:

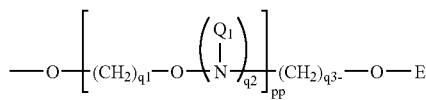

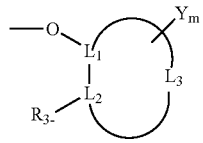

wherein

E is $C_1$-$C_{10}$ alkyl, $N(Q_1)(Q_2)$ or $N=C(Q_1)(Q_2)$;

each $Q_1$ and $Q_2$ is, independently, H, $C_1$-$C_{10}$ alkyl, dialkylaminoalkyl, a nitrogen protecting group, a tethered or untethered conjugate group, a linker to a solid support, or $Q_1$ and $Q_2$, together, are joined in a nitrogen protecting group or a ring structure that can include at least one additional heteroatom selected from N and O;

$R_3$ is $OX_1$, $SX_1$, or $N(X_1)_2$;

each $X_1$ is, independently, H, $C_1$-$C_8$ alkyl, $C_1$-$C_8$ haloalkyl, $C(=NH)N(H)Z_8$, $C(=O)N(H)Z_8$ or $OC(=O)N(H)Z_8$;

$Z_8$ is H or $C_1$-$C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $O(Q_1)$, halo, $S(Q_1)$, or CN;

each $q_1$ is, independently, from 2 to 10;

each $q_2$ is, independently, 0 or 1;

m is 0, 1 or 2;

pp is from 1 to 10; and $q_3$ is from 1 to 10 with the proviso that when pp is 0, $q_3$ is greater than 1;

$R_t$ is a phosphorus protecting group of formula:

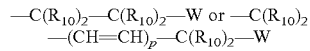

each $R_{10}$ is independently H or lower alkyl;

W is an electron withdrawing group;

p is 0 to 3;

each $Y_2$ is independently, O, $CH_2$ or NH;

each Z is independently O or S;

Each X is independently O or S;

Q is a linker connected to a solid support, —OH or O—Pr where Pr is a hydroxyl protecting group; and n is 1 to about 100;

b) contacting said sample with a deprotecting reagent for a time and under conditions sufficient to remove substantially said $R_t$ groups from said oligomers; and c) reacting said oligomers with a cleaving reagent;

wherein said deprotecting reagent comprises at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents.

Also provided by the present invention are methods for deprotecting a phosphate-linked oligomer, said oligomer having a plurality of protected phosphorus linkages of Formula II:

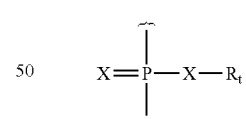

wherein X and $R_t$ are as defined above, comprising:

(a) providing a sample containing a plurality of said phosphate linked oligomers;

(b) contacting said oligomers with a deprotecting reagent for a time and under conditions sufficient to remove substantially all of said $R_t$ groups from said oligomers, said deprotecting reagent containing at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents; and (c) reacting said oligomers with a cleaving reagent.

In further embodiments, the present invention provides methods for deprotecting a phosphate-linked oligomer, said oligomer having a plurality of protected phosphorus linkages of formula II comprising:

(a) providing a sample containing a plurality of said phosphate linked oligomers;

(b) contacting said oligomers with a deprotecting reagent for a time and under conditions sufficient to remove substantially all of said $R_t$ groups from said oligomers;

(c) washing said deprotected oligomers with a washing reagent comprising at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents; and (d) reacting said oligomers with a cleaving reagent.

The present invention also provides methods for deprotecting a phosphate-linked oligomer, said oligomer having a plurality of phosphorus linkages of formula II comprising:

(a) providing a sample containing a plurality of said phosphate linked oligomers; and (b) contacting said oligomers with a deprotecting reagent for a time and under conditions sufficient to remove substantially all of said $R_t$ groups from said oligomers, said deprotecting reagent comprising gaseous ammonia.

Further provided in accordance with the present invention are methods of preparing a sample of a phosphate. linked oligonucleotide having a substantially reduced content of acrylonitrile adduct comprising:

(a) providing a sample containing a plurality of oligomers, said oligomers having a plurality of phosphorus protecting groups;

(b) contacting said oligomers with a deprotecting agent to remove substantially all of said phosphorus protecting groups from said oligomers;

said deprotecting reagent comprising at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents;

(c) optionally washing said oligomers; and (d) reacting said oligomers with a cleaving reagent.

Further provided in accordance with the present invention are methods of preparing a sample of a phosphate linked oligonucleotide having a substantially reduced content of acrylonitrile adduct comprising:

(a) providing a sample containing a plurality of oligomers, said oligomers having a plurality of phosphorus protecting groups;

(b) contacting said oligomers with a deprotecting agent to remove substantially all of said phosphorus protecting groups from said oligomers;

(c) washing said oligomers with a washing reagent, said washing reagent comprising at least one amine, the conjugate acid of said amine having a pKa of from about 8 to about 11; said deprotecting reagent optionally further comprising one or more solvents selected from the group consisting of alkyl solvents, haloalkyl solvents, cyanoalkyl solvents, aryl solvents and aralkyl solvents; and (d) reacting said oligomers with a cleaving reagent.

Thus, in some preferred methods of the invention, a support-bound or solution phase oligomer having a plurality of phosphorus protecting groups that are capable of producing acrylonitrile, or a structurally similar product that can form an adduct with nucleobase amino groups, is contacted with a deprotecting reagent that includes at least one amine. The amine is selected such that it is a sufficiently strong base to effect the removal of a substantial majority of the phosphorus protecting groups, but insufficiently strong to cause deprotonation the thymidine $N^3$ position, and hence activation of that position to adduct formation. It has been found that suitable amines include those whose conjugate acids have a pKa of from about 8 to about 11, more preferably from about 9 to about 11, even more preferably from about 10 to about 11. In general, it is preferred that the amine be an aliphatic amine of the formula $(R)_3N$, $(R)_2NH$, or $RNH_2$ where R is alkyl. Two particularly suitable amines are triethylamine and piperidine.

As used herein, the term "deprotect" or deprotection" is intended to mean the removal of the vast majority, and more preferably substantially all phosphorus protecting groups from the oligomers of interest.

In preferred embodiments, the deprotecting reagent can be either an aliphatic amine, or a solution of one or more amines aliphatic as described above. In more preferred embodiments, the deprotecting reagent further comprises one or more solvents selected from the group consisting of alkyl solvents, haloalkyl solvents, cyanoalkyl solvents, aryl solvents and aralkyl solvents. Preferably, the solvent is a haloalkyl solvent or a cyanoalkyl solvent. Examples of particularly suitable solvents are acetonitrile and methylene chloride.

In the practice of the present invention, it is greatly preferred that the vast majority of the cyanoethyl groups be removed before the oligomer is treated with the relatively strong conditions of the cleavage reagent (e.g., 30% aqueous ammonium hydroxide). The rate of deprotection of β-cyanoethyl groups from oligonucleotides has been shown to exhibit a marked solvent effect. For example, the half-life of a dimer containing a single cyanoethyl group in a 1:1 v/v solution of triethylamine in acetonitrile or methylene chloride is, very approximately, 10 min. at 25° C., whereas the half-life of the same compound in triethylamine-pyridine (1:1, v/v) is about ten times longer. Eritja et al. (*Tetrahedron*, 48, 4171-4182 (1992)) recommend a three hour treatment with a 40% solution of triethylamine in pyridine as sufficient to avoid formation of acrylonitrile adduct to thymidine residues in oligonucleotides subsequently treated with DBU. However, it has been discovered that under the conditions described by Eritja, many of the cyanoethyl protecting groups would remain intact. While not wishing to be bound by a specific theory, it is believed that subsequent treatment with ammonium hydroxide (or any other strong base such as DBU) would lead to the formation of unacceptable levels of residues having acrylonitrile adducts. Thus, in the present invention it is preferred that the solvent which is contained in the deprotection reagent not include pyridine, or similar heterocyclic base solvents that could extend the time for removal of oligomer-bound β-cyanoethyl or other electronically similar protecting groups.

At present, the detectable limit of acrylonitrile adduct by HPLC methodologies is believed to be about 0.1%. However, it is believed that the present methods provide oligomers having as little as 0.001% of such adduct. Thus, in preferred embodiments, the oligomers produced by the methods of the invention have from 0.001% to about 1% acrylonitrile adduct, with from about 0.1% to about 1% acrylonitrile adduct being more preferred, from about 0.1% to about 0.75% acrylonitrile adduct being even more preferred, and from about 0.1% to about 0.5% acrylonitrile adduct being even more preferred. In even more preferred embodiments, the oligomers are substantially free of detectable acrylonitrile adduct.

As used herein, the term "acrylonitrile adduct" refers to adducts to exocyclic nucleobase adducts that result from the acrylonitrile formed during removal of β-cyanoethyl phosphorus protecting groups, or similar adducts formed by removal of protecting groups that form electronically similar products upon removal. Representative examples of such protecting groups are those having the formula:

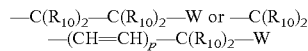
—C(R$_{10}$)$_2$—C(R$_{10}$)$_2$—W or —C(R$_{10}$)$_2$—(CH=CH)$_p$—C(R$_{10}$)$_2$—W wherein each R$_{10}$ is independently H or lower alkyl, W is an electron withdrawing group, and p is 1 to 3. The term "electron withdrawing group" is intended to have its recognized meaning in the art as a chemical moiety that attracts electron density, whether through resonance or inductive effects. Examples of electron withdrawing groups are cyano, nitro, halogen, phenyl substituted in the ortho or para position with one or more halogen, nitro or cyano groups, and trihalomethyl groups. Those of skill in the art will readily recognize other electron withdrawing groups, as well as other phosphorus protecting groups that have similar potential to form adducts with exocyclic amino or hydroxyl functions.

After contact with the deprotecting reagent, the oligomers can be further washed prior to reaction with a cleavage reagent, or reacted with the cleaving reagent directly. The cleaving reagent is a solution that includes a single reagent or combination of reagents that effect the cleavage of the deprotected oligomer from a solid support, and/or, where the oligomer is in solution, effects cleavage of exocyclic protecting groups, for example 30% aqueous ammonium hydroxide.

In the methods of the invention, it is generally advantageous to effect removal of substantially all phosphorus protecting groups from the oligomers, and separating the acrylonitrile or acrylonitrile-like products from the oligomers prior to exposing oligomers to the more severe basic conditions that effect cleavage from the solid support, or removal of exocyclic and/or hydroxyl protecting groups. Thus, in some preferred embodiments, a washing step is utilized in between contact with deprotecting reagent and cleaving reagent. In some preferred embodiments the washing step is performed using one or more suitable solvents, for example acetonitrile or methylene chloride. In other preferred embodiments, washing is performed with a washing reagent that contains one or more amines as is employed in the deprotecting reagent.

In some particularly preferred embodiments, a scavenger can be included in the deprotection reagent, cleaving reagent, washing reagent, or combinations thereof. In general, the scavenger is a molecule that reacts with the acrylonitrile or acrylonitrile-like products of deprotection, lowering the possibility of nucleobase adduct formation. Suitable scavengers include purines, pyrimidines, inosine, pyrroles, imidazoles, triazoles, mercaptans, beta amino thiols, phosphines, phosphites, dienes, ureas, thioureas, amides, imides, cyclic imides and ketones. Further useful scavengers include alkylmercaptans, thiols, ethylene glycol, substituted ethylene glycols, 1-butanethiol, S-(2-amino-4-thiazolylmethyl)isothiourea hydrochloride, 2-mercaptoethanol, 3,4-dichlorobenzylamine, benzylamine, benzylamine in the presence of carbon disulfide, hydroxylamine, 2-phenylindole, n-butylamine, diethyl ester of acetaminomalonic acid, ethyl ester of N-acetyl-2-cyanoglycine, 3-phenyl-4-(o-fluorophenyl)-2-butanone, 3,4-diphenyl-2-butanone, desoxybenzoin, -methoxyphthalimide, p-sulfobenzenediazonium chloride, p-sulfamidobenzenediazonium chloride.

In some preferred embodiments, the scavenger is a resin containing a suitable scavenging molecule bound thereto. Exemplary scavenger resins include polymers having free thiol groups and polymers having free amino groups, for example a polymer-bound amine resin wherein the amine is selected from benzylamine, ethylenediamine, diethylamine triamine, tris(2-aminoethyl)amine, methylamine, methylguanidine, polylysine, oligolysine, Agropore™ NH$_2$HL, Agropore™ NH$_2$LL, 4-methoxytrityl resin, and thiol 2-chlorotrityl resin.

The methods of the present invention are useful for the preparation of oligomeric compounds containing monomeric subunits that are joined by a variety of linkages, including phosphite, phosphodiester, phosphorothioate, and/or phosphorodithioate linkages.

As used herein, the terms "oligomer" or "oligomeric compound" are used to refer to compounds containing a plurality of nucleoside monomer subunits that are joined by internucleoside linkages, preferably phosphorus-containing linkages, such as phosphite, phosphodiester, phosphorothioate, and/or phosphorodithioate linkages. The term "oligomeric compound" therefore includes naturally occurring oligonucleotides, their analogs, and synthetic oligonucleotides.

In some preferred embodiments of the compounds of the invention, substituent W can be an electron withdrawing group selected such that it facilitates attack by a nucleophile. Accordingly, W can be any of a variety of electron withdrawing substituents, provided that it does not otherwise interfere with the methods of the invention. Preferred non-silyl electron withdrawing W groups include cyano, NO$_2$, alkaryl groups, sulfoxyl groups, sulfonyl groups, thio groups, substituted sulfoxyl groups, substituted sulfonyl groups, or substituted thio groups, wherein the substituents are selected from the group consisting of alkyl, aryl, or alkaryl. Particularly preferred are alkanoyl groups having the formula R—C(=O)— where R is an alkyl group of from 1 to six carbons, with acetyl groups being especially preferred. W can also be a trisubstituted silyl moiety, wherein the substituents are alkyl, aryl or both.

In some preferred embodiments, the scavenger is a resin containing a suitable scavenging molecule bound thereto. Exemplary scavenger resins include polymers having free thiol groups and polymers having free amino groups, for example a polymer-bound amine resin wherein the amine is selected from benzylamine, ethylenediamine, diethylamine triamine, tris(2-aminoethyl)amine, methylamine, methylguanidine, polylysine, oligolysine, Agropore™ NH$_2$HL, Agropore™ NH$_2$LL (available from Aldrich Chem. Co. St. Louis. Mo.), 4-methoxytrityl resin, and thiol 2-chlorotrityl resin.

When used as part of the cleaving reagent, contact with fluoride ion preferably is effected in a solvent such as tetrahydrofuran, acetonitrile, dimethoxyethane, or water. Fluoride ion preferably is provided in the form of one or more salts selected from tetraalkylammonium fluorides (e.g., tetrabutylammonium fluoride (TBAF)), potassium fluoride, cesium fluoride, or triethylammonium hydrogen fluoride.

The present invention is applicable to the preparation of phosphate linked oligomers having a variety of internucleoside linkages including phosphite, phosphodiester, phosphorothioate, and phosphorodithioate linkages, and other linkages known in the art In preferred embodiments, the methods of the invention are used for the preparation of oligomeric compounds including oligonucleotides and their analogs. As used herein, the term "oligonucleotide analog" means compounds that can contain both naturally occurring (i.e. "natural") and non-naturally occurring ("synthetic") moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

Representative nucleobases useful in the compounds arid methods described herein include adenine, guanine, cytosine, uracil, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30. 613-722 (see especially pages 622 and 623, and in the *Concise Encyclopedia of Polymer Science and Engineering*, J. I. Kroschwitz Ed., John Wiley & Sons, 1990, pages 858-859, Cook, P.D., *Anti-Cancer Drug Design*, 1991, 6, 585-607. The 'term nucleosidic base' is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41-50, hereby incorporated by reference in its entirety.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

As used herein, the term "alkanoyl" has its accustomed meaning as a group of formula —C(=O)-alkyl. A preferred alkanoyl group is the acetoyl group.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention oligomers can be linked connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. No. 4,725,677 and U.S. Pat. No. Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Eckstein, F. Ed., IRL Press, N.Y., 1991, Chapter 1, pages 1-23. Other linkers include the "TAMRA" linker described by Mullah et. al., *Tetrahedron Letters*, 1997, 38, 5751-5754, and the "Q-linker" described by Pon et. al., Nucleic Acid Research, 1997, 25, 3629-3635.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, Tenta-Gel Support—an aminopolyethyleneglycol derivatized support (see, e.g., Wright, et al., *Tetrahedron Letters* 1993, 34, 3373) and Poros—a copolymer of polystyrene/divinylbenzene.

In some preferred embodiments of the invention hydroxyl groups can be protected with a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., Tetrahedron 1992, 48, 2223-2311, and also in Greene and Wuts, *Protective Groups in Organic Synthesis*, Chapter 2, 2d ed, John Wiley & Sons, New York, 1991. Preferred protecting groups used for $R_2$, $R_3$ and $R_{3a}$ include dimethoxytrityl (DMT), monomethoxytrityl, 9-phenylxanthen-9-yl (Pixyl) and 9-(p-methoxyphenyl)xanthen-9-yl (Mox). The hydroxyl protecting group can be removed from oligomeric compounds of the invention by techniques well known in the art to form the free hydroxyl. For example, dimethoxytrityl protecting groups can be removed by protic acids such as formic acid, dichloro-acetic acid, trichloroacetic acid, p-toluene sulphonic acid or with Lewis acids such as for example zinc bromide. See for example, Greene and Wuts, supra.

In some preferred embodiments of the invention amino groups are appended to alkyl or to other groups such as, for example, to 2'-alkoxy groups. Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, R.P., et.al., *J. Chem. Soc.*, 1990, 112, 1253-1254, and Iyer, R.P., et.al., *J. Org. Chem.*, 1990, 55, 4693-4699); 3-methyl-1,2,4-thiazolin-5-one (MEDITH; Zong, et al., *Tetrahedron Lett.* 1999, 40, 2095); tetraethylthiuram disulfide (see e.g., Vu, H., Hirschbein, B.L., *Tetrahedron Lett.*, 1991, 32, 3005-3008); dibenzoyl tetrasulfide (see e.g., Rao, M.V., et.al., *Tetrahedron Lett.*, 1992, 33, 4839-4842); di(phenylacetyl)disulfide (see e.g., Kamer, P.C.J., *Tetrahedron Lett.*, 1989, 30, 6757-6760); Bis(O,O-diisopropoxy phosphinothioyl)disulfides (see Stec et al., *Tetrahedron Lett.*, 1993, 34, 53 17-5320); 3-ethoxy-1,2,4-dithiazoline-5-one (see *Nucleic Acids Research*, 1996 24, 1602-1607, and *Nucleic Acids Research*, 1996 24, 3643-3644); Bis(p-chlorobenzenesulfonyl)disulfide (see *Nucleic Acids Research*, 1995, 23, 4029-4033); sulfur, sulfur in combination with ligands like triaryl, trialkyl, triaralkyl, or trialkaryl phosphines.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 100 monomer subunits. It is more preferred that such compounds comprise from about 5 to about 50 monomer subunits, more preferably 10 to about 30 monomer subunits, with 15 to 25 monomer subunits being particularly preferred. When used as "building blocks" in assembling larger oligomeric compounds, smaller oligomeric compounds are preferred. Libraries of dimeric, trimeric, or higher order compounds can be prepared by the methods of the invention. The use of small sequences synthesized via solution phase chemistries in automated synthesis of larger oligonucleotides enhances the coupling efficiency and the purity of the final oligonucleotides. See for example: Miura, K., et al., *Chem. Pharm. Bull.*, 1987, 35, 833-836; Kumar, G., and Poonian, M.S., *J. Org. Chem.*, 1984, 49, 4905-4912; Bannwarth, W., *Helvetica Chimica Acta*, 1985, 68, 1907-1913; Wolter, A., et al., *nucleosides and nucleotides*, 1986, 5, 65-77.

The present invention is amenable to the preparation of oligomers that can have a wide variety of 2'-substituent groups. As used herein the term "2'-substituent group" includes groups attached to the 2' position of the sugar moiety with or without an oxygen atom. 2'-Sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)m, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P.D., *Anti-Cancer Drug Design*, 1991, 6, 585-607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, now U.S. Pat. No. 6,166,197, hereby incorporated by reference in its entirety.

Representative 2'—O— sugar substituents of formula XII are disclosed in U.S. patent application Ser. No. 09/130,973, filed Aug. 7, 1998, entitled Capped 2'-Oxyethoxy Oligonucleotides, now U.S. Pat. No. 6,172,209, hereby incorporated by reference in its entirety.

Sugars having O-substitutions on the ribosyl ring are also amenable to the present invention. Representative substitutions for ring O include S, $CH_2$, CHF, and $CF_2$, see, e.g., Secrist, et al., Abstract 21, Program & Abstracts, Tenth International Roundtable, Nucleosides, Nucleotides and their Biological Applications, Park City, Utah, Sep. 16-20, 1992.

Representative 2'—O— sugar substituents of formula XIII are disclosed in U.S. patent application Ser. No. 09/123,108, filed Jul. 27, 1998, now U.S. Pat. No. 6,271,358, entitled RNA Targeted 2'-Modified Oligonucleotides that are Conformationally Preorganized, hereby incorporated by reference in its entirety.

In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

The oligomeric compounds and compositions of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Example 1

Comparative Example

Present Invention Versus Prior Art Method of Erjita et al.

Treatment of cyanoethyl protected oligonucleotide phosphorothioates with ammonium hydroxide results in the generation of one equivalent of acrylonitrile (AN) per phosphorothioate linkage. In the presence of ammonium hydroxide a small percentage of thymidine residues react with the liberated AN to form $N^3$-cyanoethylthymidine (CN-T) residues.

Nonadecathymidinyloctadecaphosphorothioate (T-19 P=S) was synthesized and deprotected under three sets of conditions:
 (a) Ammonium hydroxide, 60° C., 16 h;
 (b) Triethylamine-pyridine (2:3 v/v), 25° C., 3 h then ammonium hydroxide, 60° C., 16 h;
 (c) Triethylamine-acetonitrile (1:1, v/v), 25° C., 12 h, then ammonium hydroxide, 60° C., 16 h.

The second set of conditions are those recommended by Erijta. The crude oligonucleotides obtained by evaporation of the ammonium hydroxide lysates were detritylated and inspected by liquid chromatography-mass spectroscopy (LC-MS) in order to quantify the amount of CN-T present. It was shown that the levels of CN-T in T-19 P=S samples subjected to conditions a), b) and c) were ca. 15%, 2% and less than 0.1%, respectively.

The results demonstrate that the conditions proposed by Erijta lead to the formation of oligonucleotides that still contain high levels of CN-T residues, where as the methods of the present invention suppress CN-T formation to a level below the detection limit of the assay.

Example 2

Synthesis of fully-modified 5'-d (TTT-TTT-TTT-TTT-TTT-TTT-T)-3' phosphorothioate 20 mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 1 minute. At the end of synthesis, the support was washed with a solution of triethylamine in acetonitrile (1:1, v/v) for 12 h, cleaved, deprotected and purified in the usual manner.

Example 3

Synthesis of fully-modified 5'-d(GCC-CAA-GCT-GGC-ATC-CGT-CA)-3' phosphorothioate 20-mer [SEQ ID NO: 2]

The synthesis of the above sequence was performed on a Pharmacia OligoPilot I Synthesizer on a 160 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with a solution of triethylamine in acetonitrile (1:1, v/v) for 12 h, cleaved, deprotected and purified in the usual manner.

Example 4

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 1 minute. At the end of synthesis, the support was transferred to a container, stirred with a solution of triethylamine in acetonitrile (1:1, v/v) for 12 h, filtered, then treated with 30% aqueous ammonium hydroxide, cleaved, deprotected and purified in the usual manner.

Example 5

Synthesis of fully-modified 5'-d(GCC-CAA-GCT-GGC-ATC-CGT-CA)-3' phosphorothioate 20-mer [SEQ ID NO: 2]

The synthesis of the above sequence was performed on a Pharmacia OligoPilot I Synthesizer on a 160 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was transferred to a container, stirred with a solution of triethylamine in acetonitrile (1:1, v/v) for 12 h, filtered, then treated with 30% aqueous ammonium hydroxide, cleaved, deprotected and purified in the usual manner.

Example 6

Synthesis of fully-modified 5'-d(TTT-TTT-TTT-TTT-TTT-TTT-T)-3' phosphorothioate 20-mer [SEQ ID NO: 2]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazolc in acetonitrile. Sulfurization was performed using a 0.2 M solution of phenylacetyl disulfide in acetonitrile:3-picoline (1:1 v/v) for 1 minutes. At the end of synthesis, the support was taken in 30% aqueous ammonium hydroxide along with thymidine, cleaved, deprotected and purified in the usual manner.

Example 7

Synthesis of fully-modified 5'-d(GCC-CAA-GCT-GGC-ATC-CGT-CA)-3' phosphorothioate 20-mer [SEQ ID NO: 2]

The synthesis of the above sequence was performed on a Pharmacia OligoPilot I Synthesizer on a 160 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was taken in 30% aqueous ammonium hydroxide along with thymidine, cleaved, deprotected and purified in the usual manner.

Example 8

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 1 minute. At the end of synthesis, the support was taken in 30% aqueous ammonium hydroxide along with uridine, cleaved, deprotected and purified in the usual manner.

Example 9

Synthesis of fully-modified 5'-d(GCC-CAA-GCT-GGC-ATC-CGT-CA)-3' phosphorothioate 20-mer [SEQ ID NO: 2]

The synthesis of the above sequence was performed on a Pharmacia OligoPilot I Synthesizer on a 160 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was taken in 30% aqueous ammonium hydroxide along with uridine, cleaved, deprotected and purified in the usual manner.

Example 10

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile: 3-picoline (1:1 v/v) for 1 minutes. At the end of synthesis, the support was taken in 30% aqueous ammonium hydroxide along with imidazole, cleaved, deprotected and purified in the usual manner.

Example 11

Synthesis of fully-modified 5'-d(GCC-CAA-GCT-GGC-ATC-CGT-CA)-3' phosphorothioate 20-mer [SEQ ID NO: 2]

The synthesis of the above sequence was performed on a Pharmacia OligoPilot I Synthesizer on a 160 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was taken in 30% aqueous ammonium hydroxide along with imidazole, cleaved, deprotected and purified in the usual manner.

Example 12

GMP Manufacture of fully-modified 5'-d(GCC-CAA-GCT-GGC-ATC-CGT-CA)-3' phosphorothioate 20-mer [SEQ ID NO: 2] (ISIS 2302) on OligoProcess ISIS 2302 [5'-d(GCC-CAA-GCT-GGC-ATC-CGT-CA)-3'] [SEQ ID NO: 2] was manufactured under Good Manufacturing Practice (GMP) conditions on a Pharmacia OligoProcess Synthesizer on a 150 mmole scale using the cyanoethyl phosphoramidites obtained from Pharmacia and Pharmacia's HL 30 primary support. Detritylation was performed using 3% dichioroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with a solution of triethylamine in acetonitrile (1:1, v/v) for 30 minutes and then let stand at room temperature overnight, filtered, washed with acetonitrile solvent and then treated with 30% aqueous ammonium hydroxide, cleaved, deprotected and purified in the usual manner. The oligonucleotide was analyzed by mass spectroscopy to confirm the elimination of acrylonitrile adduct.

Example 13

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with thymidine nucleoside (20 equivalents), deprotected and purified in the usual manner.

Example 14

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with uridine nucleoside (20 equivalents), deprotected and purified in the usual manner.

Example 15

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with inosine nucleoside (20 equivalents), deprotected and purified in the usual manner.

Example 16

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with thymine (25 equivalents), deprotected and purified in the usual manner.

Example 17

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with uracil (25 equivalents), deprotected and purified in the usual manner.

Example 18

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with imidazole (50 equivalents), deprotected and purified in the usual manner.

Example 19

Synthesis of fully-modified 5'-d(TTT-TTT-TTT-TTT-TTT-TTT-T)-3' phosphorothioate 20-mer [SEQ ID NO: 1]

The synthesis of the above sequence was performed on a Pharmacia OligoPilot I Synthesizer on a 30 micromole scale using the cyanoethyl phosphoramidites obtained from Pharmacia and Pharmacia's HL 30 primary support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was incubated with benzyl mercaptan (50 equivalents), deprotected and purified in the usual manner.

Examples 20-27

Oligonucleotide Synthesis.

Oligodeoxynucleotides were assembled on an ABI 380B DNA Synthesizer using 5'—O—(4,4'-dimethoxytrityl) nucleoside 3'—O—(carboxymethyloxy)acetate derivatized CPG 1 (shown in Scheme 1 below) phosphoramidite chemistry, and either commercial oxidizer or 3H-1,2-benzodithiol-3-one 1,1-dioxide (0.05 M in MeCN) as the sulfur-transfer reagent.

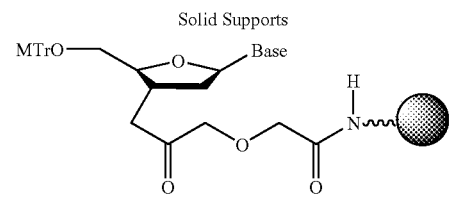

Scheme 1

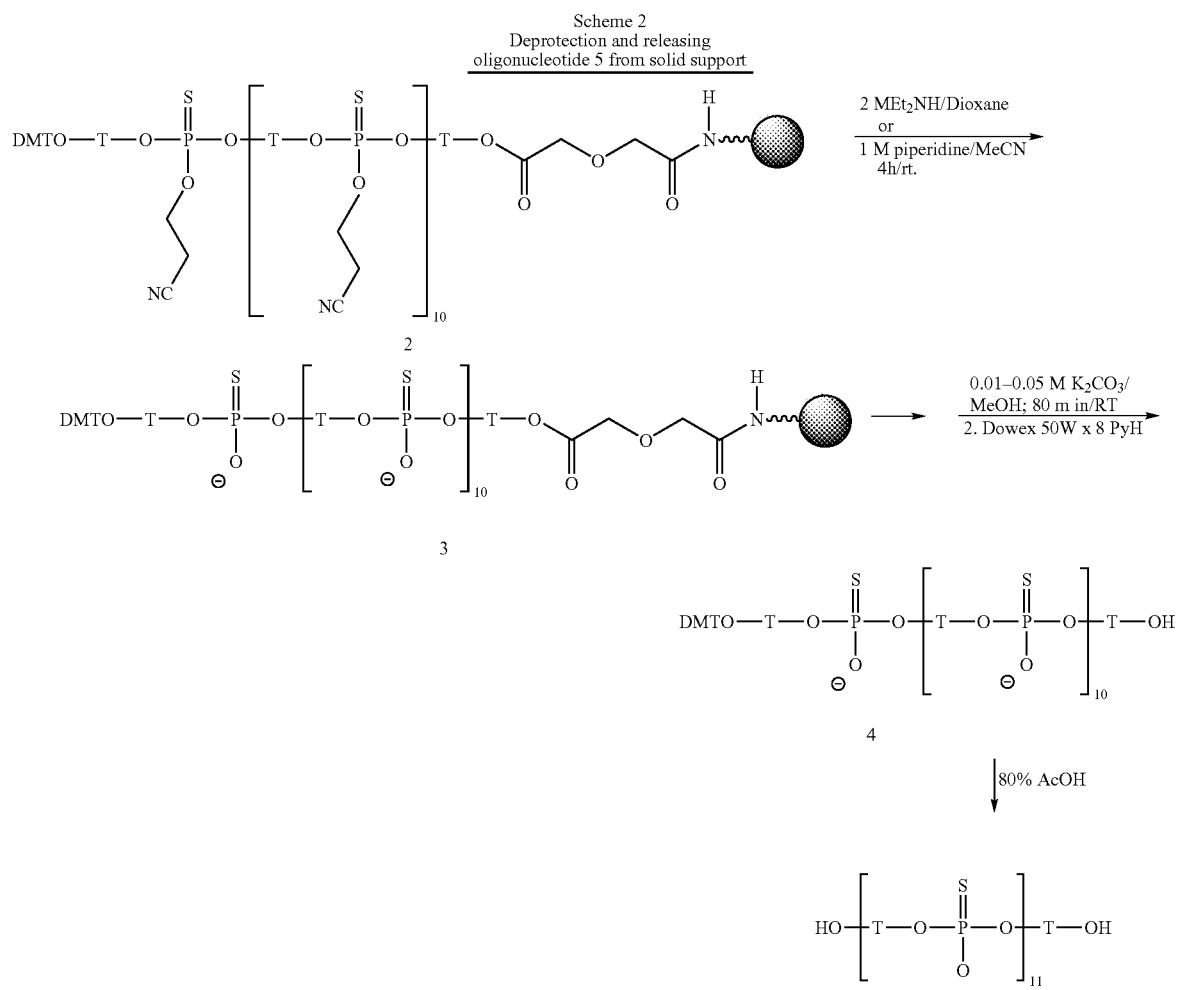

Scheme 2
Deprotection and releasing oligonucleotide 5 from solid support

Deoxynucleoside CE phosphoramidites protected in a standard manner ($A^{bz}$, $C^{bz}$, $G^{ib}$) were used to synthesize oligonucleotides presented in Examples 21, 23-27. Those used for the preparation of oligonucleotides presented in Examples 20 and 22 were uniformly protected with either phenoxyacetyl (PAC) or 4-(t-butyl)phenoxyacetyl (tBPA) groups.

Example 20

Two Step Deprotection of Oligonucleotideas with Secondary Amines in an Organic Solvent Followed by Methanolic $K_2CO_3$.

Deprotection procedure is exemplified on Scheme 2 for dodecathymidylate 5. After completeness of oligonucleotide synthesis a solid support-bound 2 was decyanoethylated with either 2M diethylamine or 1M piperidine in MeCN, dioxane, THF, or DMF (3 mL) for 2 to 12 h. The column was washed with dioxane (10 mL) to give 3. Other amines, for instance, morpholine, pyrrolidine, or dimethylamine can also be used on this step.

The oligonucleotide 4 was released from the solid support 3 by treatment with 0.01 to 0.05 M $K_2CO_3$ in MeOH (2'5 mL and 2'20 mL for 1 and 15 mmol syntheses, respectively). Each portion was passed forth and back through the column for 45 min, neutralized by passing through short column with Dowex 50W'8 (PyH+; ca. 1 mL). The combined eluates were evaporated to dryness, co-evaporated with MeCN (10 mL), and dissolved in water. Target oligonucleotide 4 was isolated by RP HPLC on a Delta Pak 15 mm C18 300Å column (3.9×300 mm and 7.8×300 mm for 1 and 15 mmol syntheses, respectively), using 0.1 M $NH_4OAc$ as buffer A, 80% aq MeCN as buffer B, and a linear gradient from 0 to 60% B in 40 min at a flow rate 1.5 and 5 mL $min^{-1}$, respectively. Collected fractions were evaporated and detritylated with 80% aq AcOH for 30 min at room temperature. The solvent was evaporated, the product was re-dissolved in water and desalted by injecting on to the same column, then washing with water (10 min) and eluting an oligonucleotide 5 as an ammonium salt with 50% aq MeCN (20 min). Homogeneity of 5 was characterized by RP HPLC and capillary electrophoresis. ESMS: 3764.2 (found); 3765.1 (calculated)

The efficiency of the deprotection method was verified in preparation of oligonucleotide phosphorothioates 6 and 7 (Isis 1939) and phosphodiester oligonucleotide 8 in 1 to 15 mmol scale.

6: $C_5A_2T_{11}$ [SEQ ID NO: 3] thioate. ESMS: 5628.3 (found); 5629.6 (calculated).
7: $C_5AC_2ACT_2C_4TCTC$ [SEQ ID NO: 4] thioate. ESMS: 6438.6 (found); 6440.2 (calculated).
8: $C_5A_2T_{11}$. [SEQ ID NO: 3] ESMS: 5355.8 (found); 5356.4 (calculated).

Example 21

Two step deprotection of oligonucleotide TGCATC$_5$AG$_2$C$_2$AC$_2$AT [SEQ ID NO: 5] (9) with secondary amines in an organic solvent followed by ammonolysis.

A solid support-bound oligonucleotide was decyanoethylated with either 2M diethylamine or 1M piperidine, morpholine, or diethylamine in MeCN, dioxane, THF, or DMF as described in Example 20. Other amines, for instance, morpholine, pyrrolidine, or dimethylamine can also be used on this step.

The solid support was treated with conc. aq ammonia for 2 h at room temperature, the solution was collected and kept at 55° C. for 8 h. On removal of solvent, the residue was re-dissolved in water and purified as described in Example 20.

9: ESMS: 5980.9 (found); 5982.8 (calculated).
10: TGCATC$_5$AG$_2$C$_2$AC$_2$AT [SEQ ID NO: 5] thioate. ESMS: 6287.8 (found); 6288.0 (calculated).

Example 22

Deprotection of Synthetic Oligonucleotides with Aqeous Amines.

Deprotection procedure is exemplified for oligonucleotide 10. A solid support-bound material (20 μmol) was treated with 1 M aq piperidine for 2 h at room temperature. Other amines, for instance, morpholine, pyrrolidine, diethylamine, dimethylamine, ethylamine, or methylamine can also be used on this step. The solid support was washed with another portion of the deprotecting reagent, and combined solutions were evaporated under reduced pressure. Crude 5'-DMTr protected oligonucleotide was dissolved in water (5 mL) and purified by semipreparative HPLC on a DeltaPak C18 column (Waters, 15 mm; 300 Å; 25'100 mm) using 0.1 M NH$_4$OAc as buffer A, 80% aq MeCN as buffer B, and a linear gradient from 0 to 40% B in 50 min at a flow rate 15 mL min$^{-1}$. Collected fractions were evaporated, the residue was treated with 80% aq AcOH for 30 min and evaporated to dryness. The obtained material was dissolved in 50% aq DMSO and loaded onto the same column. The column was washed with 0.05 M aq NaOAc (15 min) and water (15 min) at a flow rate 15 mL min$^{-1}$. Elution with 60% aq MeCN and evaporation to dryness gave 23.0 mg (20%) of desalted oligonucleotide 10 (Na$^+$ salt), ESMS: 6286.4 (found); 6288.0 (calculated).

Example 23

Deprotection of Synthetic Oligonucleotides with Aqueous Secondary Amines.

On completeness of oligonucleotide synthesis, a solid support-bound material (20 mmol) was treated with an aq amine as described in Example 22. On evaporation of the solution of the deprotecting reagent, the residue was treated with ammonium hydroxide for 8 h at 55° C., and the solvent was evaporated. The product, 6, was isolated and characterized as described in Example 22.

Example 24

Deprotection of Synthetic Oligonucleotides with Ammonia in the Presence of Aminoalkyl Resins as Acrylonitrile Scavengers. Method A.

On completeness of oligonucleotide synthesis, a solid support-bound material (20 mmol) is mixed with an aminoalkyl resin [for instance, aminoalkyl CPG or polymer-bound tris(2-aminoethyl)amine] and treated with conc. aq ammonia for 2 h at room temperature. The solid phase is filtered off, and the deprotection is completed by keeping the solution at 55° C. for 8 h. The solvent was evaporated, and the product is isolated and characterized as described in Example 22.

Example 25

Deprotection of Synthetic Oligonucleotides with Ammonia in the Presence of Aminoalkyl Resins as Acrylonitrile Scavengers. Method B.

A solid support-bound material (20 mmol) is treated with a flow of conc. aq ammonia for 2 h at room temperature. On leaving the reaction vessel, the solution is passed through a second column that contained an aminoalkyl resin as in Example 24, and collected. Optionally, the collected solution may be recycled by passing again through both columns. When the releasing of oligonucleotide from CPG is complete, the oligonucleotide solution is collected and treated as in Example 24.

Example 26

Deprotection of Synthetic Oligonucleotides with Ammonia in the Presence of Morcaptanes as Acrylonitrile Scavengers.

A solid support-bound oligonucleotide was treated with conc. aq ammonia and thiocresol (0.1 M) for 2 h at room temperature, the solution was collected and kept at 55° C. for 8 h. On removal of solvent, the residue was re-dissolved in water and extracted twice with methylene chloride. The aqueous layer was collected, and the product, 5, was isolated and characterized as described in Example 20. Other thiols, for instance, thiophenol, mercaptoethanol, 1,3-ethanedithiol, or ethanethiol can also be used as acrylonitrile scavengers.

Example 27

Deprotection of Synthetic Oligonucleotides with Ammonia in the Presence of Mercaptoalkylated Resins as Acrylonitrile Scavengers.

A solid support-bound oligonucleotide is treated as in Example 25, but the second column contains a mercaptoalkylated resin (for instance, reported previously mercaptoalkylated resins[1] or NovaSyn$^0$ TG thiol resin). The product is isolated and characterized as described in Example 20.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method of preparing a phosphorus-linked oilgonucleotide comprising:

providing a sample containing a plurality of oligonucleotides, said oligonucleotides linked to a solid support medium, said oligonucleotides comprising a plurality of nucleosides and a plurality of protected phosphorus linkages;

contacting said oligonucleotides with a deprotecting agent to remove phosphorus protecting groups from said oligonucleotides, wherein said oligonucleotides remain linked to said solid support medium during said contacting;

said deprotecting reagent comprising at least one secondary amine, the conjugate acid of said secondary amine having a pKa of from about 8 to about 11;

optionally washing said oligonucleotides; and reacting said oligonucleotides with a cleaving reagent, whereby the oligonucleotides are cleaved from the solid support medium.

2. The method of claim 1, wherein the secondary amine is an aliphatic amine.

3. The method of claim 2, wherein the aliphatic amine is $(R)_2NH$, where R is alkyl.

4. The method of claim 3, wherein R is ethyl.

5. The method of claim 1, wherein at least one of the phosphorus protecting groups is a cyanoethyl protecting group.

6. The method of claim 1, wherein at least one of said nucleosides has a 2' substituent group selected from O-alkyl or fluoro.

7. A method for deprotecting a phosphorus-linked oligonucleotide comprising a plurality of nucleosides and a plurality of protected phosphorus linkages of Formula II:

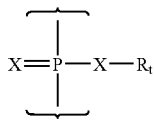

wherein:
each X is O or S;
$R_t$ is a phosphorus protecting group of formula:

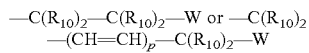

each $R_{10}$ is independently H or lower alkyl;
W is cyano;
p is 1 to 3
said oligonucleotides being linked to a solid support medium, the method comprising:
providing a plurality of said phosphorus-linked oligonucleotides;
contacting said oligonucleotides with a deprotecting reagent for a time and under conditions sufficient to remove said $R_t$ groups from said oligonucleotides, wherein said oligonucleotides remain linked to said solid support medium during said contacting;
said deprotecting reagent comprising at least one secondary amine, the conjugateacid of said secondary amine having a pKa of from about 8 to about 11; and
optionally washing said oligonucleotides;
reacting said oligonucleotides with a cleaving reagent, whereby the oligonucleotides are cleaved from the solid support medium.

8. The method of claim 7, wherein $R_t$ is $—CH_2CH_2—CN$.

9. The method of claim 7, wherein the secondary amine is an aliphatic amine.

10. The method of claim 9, wherein the aliphatic amine is $(R)_2NH$, where R is alkyl.

11. The method of claim 7, wherein at least one of the phosphorus protecting groups is a cyanoethyl protecting group.

12. The method of claim 7, wherein at least one of said nucleosides has a 2'-substiuent group selected from O-alkyl or fluoro.

* * * * *

UNITED STATES PATENT AND TRADEMARK OFFICE
CERTIFICATE OF CORRECTION

| | | |
|---|---|---|
| PATENT NO. | : 7,227,016 B2 | Page 1 of 1 |
| APPLICATION NO. | : 11/024958 | |
| DATED | : June 5, 2007 | |
| INVENTOR(S) | : Vasulinga T. Ravikumar et al. | |

It is certified that error appears in the above-identified patent and that said Letters Patent is hereby corrected as shown below:

Column 34, Claim 7, line 1, please insert --;-- after "3".

Signed and Sealed this

Twenty-fourth Day of July, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 1
tttttttttt tttttttt                                                    19

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 2
gcccaagctg gcatccgtca                                                  20

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide

<400> SEQUENCE: 3
cccccaattt tttttttt                                                    18

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
cccccaccac ttcccctctc                                                  20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
tgcatccccc aggccaccat                                                  20